US00PP16889P3

(12) United States Plant Patent

Hildebrant, Jr.

(10) Patent No.: US PP16,889 P3

(45) Date of Patent: Jul. 25, 2006

(54) *VIBURNUM* PLANT NAMED 'C.A. HILDEBRANT'S'

(50) Latin Name: *Viburnum wrightii*
Varietal Denomination: C.A. Hildebrant's

(75) Inventor: Charles A. Hildebrant, Jr., Oldwick, NJ (US)

(73) Assignee: CP Delaware, Inc., Wilmington, DE (US)

( * ) Notice: Subject to any disclaimer, the term of this patent is extended or adjusted under 35 U.S.C. 154(b) by 54 days.

(21) Appl. No.: 10/989,322

(22) Filed: Nov. 17, 2004

(65) Prior Publication Data

US 2006/0107429 P1 May 18, 2006

(51) Int. Cl.
*A01H 5/00* (2006.01)

(52) U.S. Cl. ..... Plt./226

(58) Field of Classification Search ..... Plt./226
See application file for complete search history.

*Primary Examiner*—Kent Bell
*Assistant Examiner*—Louanne Krawczewicz Myers
(74) *Attorney, Agent, or Firm*—Buchanan Ingersoll PC

(57) ABSTRACT

The new *Viburnum wrightii* cultivar is provided that was created through an extensive controlled crossing and selection program using unreleased and unnamed parent plants. The growth habit is very dense and compact. Attractive dense relatively flat clusters of white flowers commonly are produced during mid-May to early June. Also, attractive red berries of unusually long persistence are formed. The cold hardiness is good. The new cultivar is well suited to provide attractive colorful ornamentation in gardens and in the landscape over an extended period of time.

3 Drawing Sheets

Botanical/commercial classification: *Viburnum wrightii/ Viburnum* Plant.
Varietal denomination: cv. 'C.A. Hildebrant's'.

SUMMARY OF THE INVENTION

*Viburnum* plants are recognized to be a varied and diversified group of shrubs that are widely grown to provide ornamentation. They are appreciated for their white, cream and sometimes pink spring flowers, good foliage, interesting shape, colored fruit that attracts birds, and their showy autumn color.

A new and distinct Wright *Viburnum* (i.e., *Viburnum wrightii*) plant is provided that is the product of the controlled crossing and selection program of *Viburnum wrightii* plants (unreleased, unnamed, and non-patented in the United States) at Oldwick, N.J., U.S.A., that was begun in the mid-1940's. Throughout the program the progeny were studied and were evaluated primarily for consistent berry set, growth habit, and flower production. This program resulted in the production of fifteen field grown plants from which a single plant as described herein was ultimately selected.

It was found that the new *Viburnum wrightii* plant of the present invention possesses the following combination of characteristics:

(a) displays a very dense and compact growth habit, (b) produces in abundance during mid-May to early-June attractive dense relatively flat clusters of white flowers, (c) forms attractive red berries of long persistence, and (d) displays good cold hardiness.

The new cultivar of the present invention can be readily distinguished from other *Viburnum wrightii* plants in view of the recited combination of characteristics. The brilliant fall foliage coloration and the long lasting berry set are particularly noteworthy and provide additional seasonal interest. In the fall the foliage commonly turns red, amber and maroon. The plant has well withstood temperatures as low as −10° F. without harm.

When compared to its parental plants, the new cultivar of the present invention displays glossy foliage unlike its parents, and forms considerably larger berries. Also, the parental plants display a mature height of approximately 12 feet. This can be compared to a lesser mature height of approximately 4 to 5 feet for the new cultivar of the present invention.

The new cultivar also can be readily distinguished from the *Viburnum dilatatum* 'Cardinal Candy' (non-patented in the United States) and *Viburnum dentatum* 'Christom' (non-patented in the United States) cultivars. More specifically, the 'Cardinal Candy' cultivar displays a larger plant size at maturity, a lesser berry retention time, and smaller leaves. The 'Christom' cultivar forms dissimilar rich blue berries in the fall that are retained on the plant for a lesser period of time.

The new cultivar is well suited to provide attractive colorful ornamentation in gardens and in the landscape over an extended period of time.

Asexual reproduction of the new cultivar at Oldwick, N.J., U.S.A., by the rooting of cuttings has demonstrated that the distinctive characteristics of the new cultivar of the present invention are reliably transmitted in a stable manner from one generation to another. Accordingly, the new cultivar reproduces in a true-to-type manner by such technique.

The new cultivar has been named 'C.A. Hildebrant's'.

BRIEF DESCRIPTION OF THE PHOTOGRAPHS

The accompanying photographs show as true as it is reasonably possible to make the same in color illustrations of this character typical specimens of the plant and plant parts of the new cultivar of the present invention. The depicted plants were approximately four years of age and were growing outdoors under full sun at West Grove, Pa., U.S.A.

DETAILED DESCRIPTION

Figure 1:
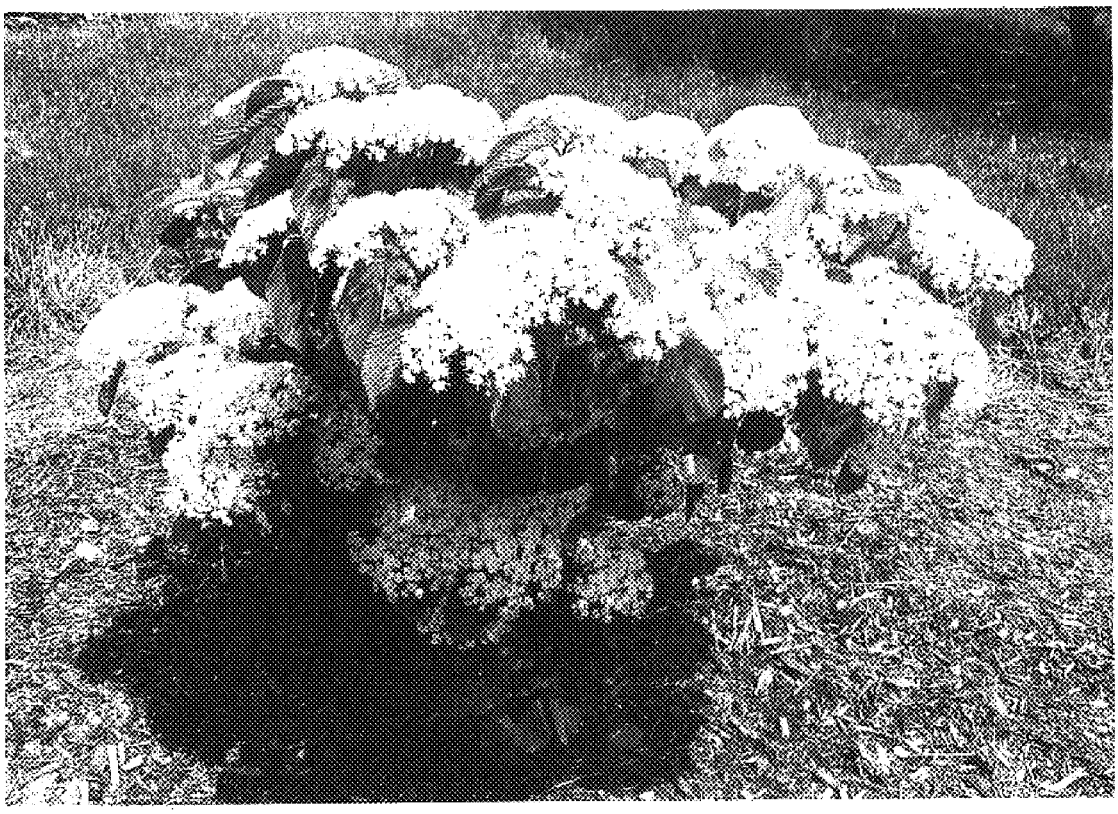
FIG. 1 shows an overall flowering plant of the new cultivar wherein the very dense and compact growth habit and the abundant presence of attractive dense relatively flat clusters of white flowers are shown.

The following description is based upon the observation of four-year-old plants of the new cultivar while growing in an outdoor garden in full sun at West Grove, Pa., U.S.A. The chart used in the identification of the colors is The R.H.S. Colour Chart of The Royal Horticultural Society, London, England.

Plant:

*Height.*—Approximately 4 to 5 feet.

*Width.*—Approximately 3 feet.

*Growth habit.*—Very dense and compact.

*Branches.*—Slender, slightly rough in texture, Grey-Brown Group 199C in coloration, commonly approximately 30 cm in length on average, commonly approximately 7 mm in diameter on average at the widest point, and commonly approximately 150 branches are present per plant on average.

*Lenticels.*—Commonly approximately 1 mm in diameter, commonly approximately 4 or 5 lenticels per cm, and near Greyed-Yellow Group 161D in coloration.

*Internode length.*—Commonly approximately 11 cm on average.

Foliage:

*Arrangement.*—Opposite, single.

*Quantity.*—Abundant, with a mature plant commonly bearing approximately 600 leaves on average.

*Mature length.*—Approximately 13 cm on average.

*Mature width.*—Approximately 8 cm at the widest point on average.

Figure 3:
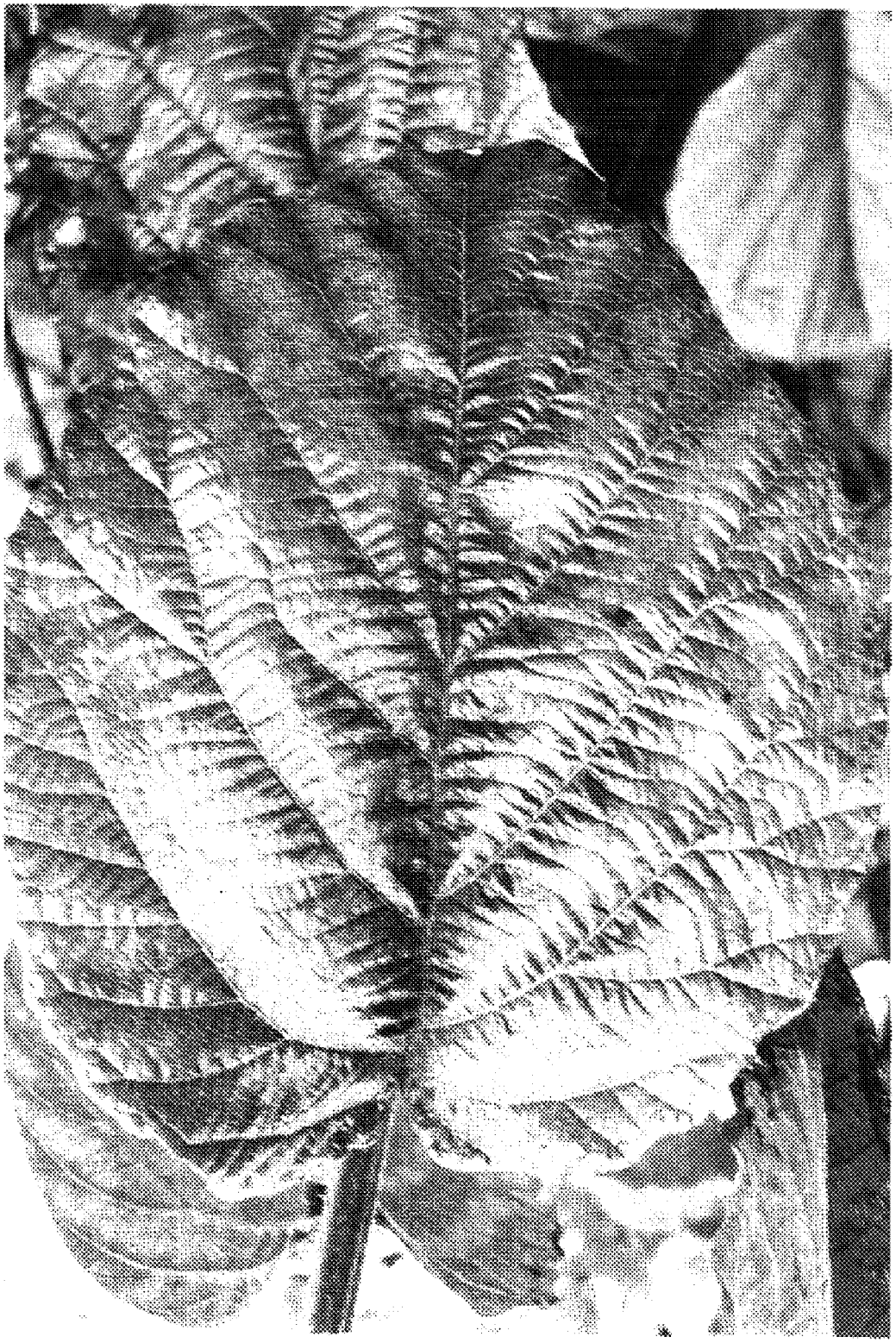
FIG. 3 shows a close enlarged view of a typical leaf during early fall. Some bright fall coloration has begun to appear primarily on a leaf in the background at the upper left portion of the photograph.

*Shape.*—Broad-elliptic as illustrated in FIG. 3.

*Apex.*—Generally obtuse.

*Base.*—Cordate.

*Margin.*—With slight crenation as illustrated in FIG. 3.

*Venation pattern.*—Commonly with 6 to 7 vein pairs emerging from a central vein to create a very branched pattern as illustrated in FIG. 3. The central vein is approximately 3 mm wide at the widest point and extends from the base to the apex of the leaf. The side veins at the base of the leaf commonly range from approximately 0.5 to 1 mm in width.

*Vein color.*—On the upper surface Yellow-Green Group 146D and on the lower surface Yellow-Green Group 148D.

*Texture.*—Glabrous and glossy on the upper surface.

*Thickness.*—Medium.

*Summer color.*—Mature leaf. Upper surface: Green Group 131A. Under surface: Green Group 138A.

*Fall color.*—Commonly a brilliant blend of red, amber, and maroon in October that is maintained well into November.

*Petiole.*—Approximately 2 cm in length, approximately 5 mm in diameter, and Yellow-Green Group 147B in coloration.

*Glands.*—None observed.

*Stipules.*—None observed.

Inflorescence:

*Description.*—In abundance in relatively flat clusters of compound cymes with approximately 20 to 25 flowers per cyme that are reminiscent of Queen Ann's Lace as illustrated in FIG. 1. Commonly, approximately 10 cymes are present per compound cyme, and typically two compound cymes are present per lateral branch.

*Flowering time.*—Commonly mid-May to early June. A first bloom has been observed on May 15$^{th}$ with full bloom on June 5$^{th}$.

*Longevity.*—Approximately 3 weeks.

*Quantity.*—The number varies with the size and age of the plant. The flowers per inflorescence commonly number approximately 240 on young plants and approximately 550 on mature plants.

*Fragrance.*—Sweet and musty.

*Sepals.*—None observed.

*Buds.*—Shape: narrow-pointed. Size: approximately 0.5 cm in length and approximately 0.2 cm in width. Color: commonly between White Group 155A and 155B.

*Compound cyme diameter.*—Relatively flat compound cymes in a cluster commonly measuring approximately 9.5 cm in diameter on average.

*Cyme depth.*—Approximately 6 cm on average.

*Flower size.*—Commonly approximately 6 mm in diameter on average and approximately 2 mm in depth on average.

*Petal number.*—Five fused petals.

*Petal shape.*—Ovate, rounded apex, and an entire margin.

*Petal length.*—Approximately 3 mm.

*Petal width.*—Approximately 2 mm.

*Petal color.*—Near White Group 155D on both surfaces.

*Stamen.*—Five in number, and approximately 5 mm in length.

*Filaments.*—Approximately 4.2 mm in length and White Group 155D in coloration.

*Anthers.*—Approximately 0.8 mm in size, regularly arranged around the style, and Yellow-Orange Group 20B in coloration.

*Pollen.*—Commonly formed in each flower in a minute quantity and Yellow-Orange Group 22A in coloration.

*Pistil.*—One per flower, 1 mm in length.

*Style.*—Columnar, short and approximately 3.2 mm in length, and White Group 155D in coloration.

*Stigma.*—Generally flattened with three lobes and White Group 155A in coloration.

*Pedicel.*—Commonly approximately 2.5 mm in length on average, approximately 1 mm in diameter, and Green Group 143C in coloration.

Fruit:

*Bearing onset.*—Commonly September to late October.

Figure 2:
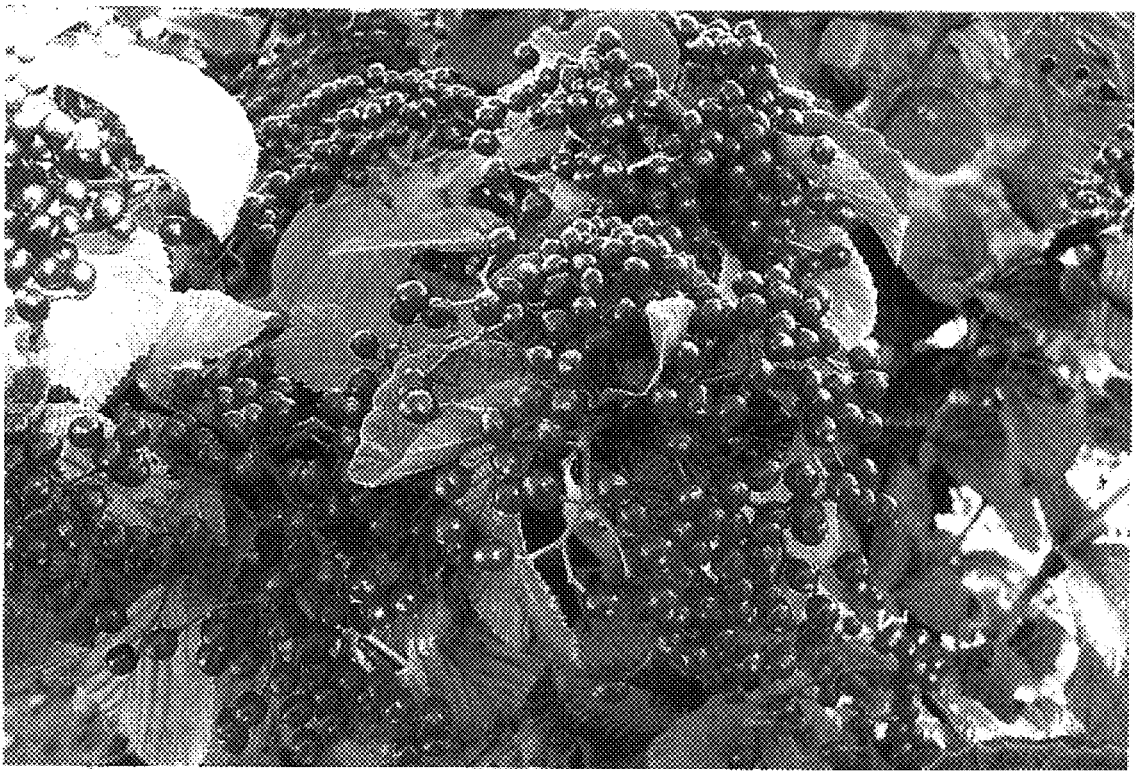
FIG. 2 shows a close view of the abundant presence of bright red berries and the foliage during early fall.

*Quantity.*—Moderately abundant as illustrated in FIG. 2, and commonly approximately 80 fruits per cluster on average.

*Size.*—Generally round and approximately 7 mm in diameter.

*Color.*—When ripe bright red, Red Group 46B, and when fully mature darkening to near Red Group 53A.

*Persistence.*—The berries commonly are retained on the plant for six months or more and generally longer than previously known plants of the species.

*Seeds.*—Typically one per fruit, obatus in shape, approximately 6 mm in length on average, approximately 5 mm in diameter on average, and Yellow-Orange Group 22A in coloration.

The new cultivar has been found to grow well in U.S.D.A. Hardiness Zone No. 6.

No particular disease or pest problem has been encountered during observations to date.

The new 'C.A. Hildebrant's' cultivar has not been observed to date under all possible environmental conditions. Accordingly, it is possible that the phenotype may vary somewhat with variations in the environment, such as temperature, light intensity, day length, and other cultural conditions without variance of the genotype. For instance, leaf coloration may vary with the composition and concentration of the fertilizer that is utilized.

I claim:

1. A new and distinct *Viburnum wrightii* plant having the following combination of characteristics:

(a) displays a very dense and compact growth habit, (b) produces in abundance during mid-May to early-June attractive dense relatively flat clusters of white flowers, (c) forms attractive bright red berries of long persistence, and (d) displays good cold hardiness;

substantially as illustrated and described.

* * * * *